US008157723B2

(12) United States Patent
Nan

(10) Patent No.: US 8,157,723 B2
(45) Date of Patent: Apr. 17, 2012

(54) MANNEQUIN WITH AN IMPROVED ATTACHMENT BETWEEN AN ARTIFICIAL ORGAN AND A TORSO OF THE MANNEQUIN

(75) Inventor: Simon Siu Man Nan, Ontario (CA)

(73) Assignee: Nanma Manufacturing Co., Ltd., Hong Kong (HK)

( * ) Notice: Subject to any disclaimer, the term of this patent is extended or adjusted under 35 U.S.C. 154(b) by 1419 days.

(21) Appl. No.: 11/712,091

(22) Filed: Feb. 28, 2007

(65) Prior Publication Data

US 2008/0207991 A1 Aug. 28, 2008

(51) Int. Cl.
*A61F 5/00* (2006.01)

(52) U.S. Cl. ........................................................ 600/38

(58) Field of Classification Search .............. 600/38–41; 128/897–898; 434/262, 267, 272–275; 446/370, 446/373, 385

See application file for complete search history.

(56) References Cited

U.S. PATENT DOCUMENTS

| | | | | |
|---|---|---|---|---|
| 5,076,261 | A | 12/1991 | Black | |
| 5,466,235 | A * | 11/1995 | Shubin, Sr. | 600/38 |
| 6,890,293 | B2 | 5/2005 | Kobayashi | |
| 7,510,537 | B2 * | 3/2009 | Imboden et al. | 601/70 |
| 2005/0033113 | A1 * | 2/2005 | Bonthuys | 600/38 |

* cited by examiner

*Primary Examiner* — John Lacyk

(74) *Attorney, Agent, or Firm* — Solsinelli Shughart PC

(57) ABSTRACT

Embodiments of the presently described invention provide a mannequin including a torso, an artificial organ and a plurality of rings. The artificial organ includes first and second openings and a channel connecting the two openings. The rings connect the artificial organ to the torso. Embodiments of the presently described invention also provide an apparatus for connecting an artificial organ to a mannequin torso. The apparatus includes a plurality of rings a plurality of holes in a torso. The rings are attached to the organ and the holes in the torso. The rings are attached to the organ proximate two openings in the organ. Embodiments of the presently described invention also provide a method for attaching an artificial organ to a mannequin. The method includes attaching a plurality of rings to the organ and attaching the rings to the mannequin.

20 Claims, 6 Drawing Sheets

MANNEQUIN WITH AN IMPROVED ATTACHMENT BETWEEN AN ARTIFICIAL ORGAN AND A TORSO OF THE MANNEQUIN

BACKGROUND OF THE INVENTION

The presently described invention generally relates to mannequins. More specifically, embodiments of the presently described invention provide an improved mannequin with organs that have a more realistic feel and are mounted on or attached to the mannequin shell in a more reliable manner than existing mannequins.

Many mannequins used for sexual purposes exist today. The main use of these mannequins is to simulate human body functions during intercourse. It is desirable that these mannequins are in the form of human body which has sexual organs with the appearance and the tactile feeling closer to those of the real human body. For this reason, these mannequins typically include artificial organs located in the crotch of the mannequin torso.

In order to achieve increased realism, the parts of the main mannequin body and the artificial organs of the mannequin should have different elasticity and tactile feels. To meet this goal, different materials inevitably must be used. That is, different materials must be used to make the mannequin body or torso and the organs.

Some of the existing mannequins include torsos having an outer shell and an internal inflatable chamber so that the outer shell (and thus the torso) has some stiffness when compared to the internal inflatable chamber. That is, the material(s) used to create the torso is stiffer than the material(s) used to create the internal inflatable chamber.

With this stiff outer shell arrangement, a problem exists for directly mounting or attaching the artificial organ(s) to the torso. That is, a reliability problem arises for mounting or attaching an object formed of a soft material on or to an object formed of a stiffer material. Currently available ways of mounting or attaching soft, artificial organs to stiffer torso shells are not reliable and frequently fail. Thus, a need exists for an improved mannequin with artificial organs that feel realistic but are mounted or attached to the mannequin torso shell in a more reliable manner.

BRIEF SUMMARY OF THE INVENTION

Embodiments of the presently described invention provide a mannequin including a torso, an artificial organ and a plurality of rings. The artificial organ includes first and second openings and a channel connecting the two openings. The rings connect the artificial organ to the torso.

Embodiments of the presently described invention also provide an apparatus for connecting an artificial organ to a mannequin torso. The apparatus includes a plurality of rings a plurality of holes in a torso. The rings are attached to the organ and the holes in the torso. The rings are attached to the organ proximate two openings in the organ.

Embodiments of the presently described invention also provide a method for attaching an artificial organ to a mannequin. The method includes attaching a plurality of rings to the organ and attaching the rings to the mannequin.

Figure 1:
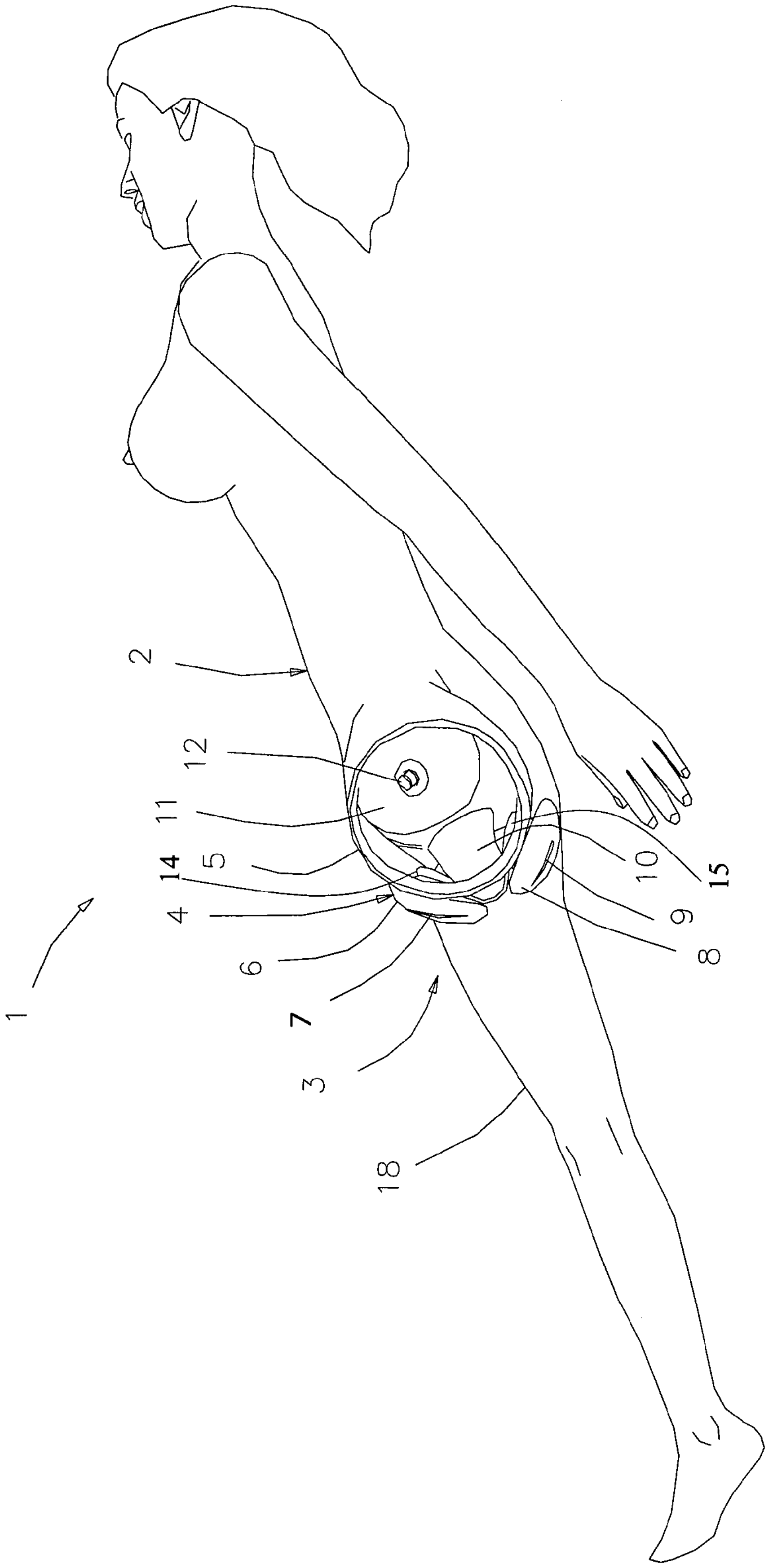
FIG. 1 illustrates a perspective view of a mannequin with one leg removed from the torso of the mannequin in accordance with an embodiment of the presently described invention.

The foregoing summary, as well as the following detailed description of certain embodiments of the presently described invention, will be better understood when read in conjunction with the appended drawings. For the purpose of illustrating the presently described technology, certain embodiments are shown in the drawings. It should be understood, however, that the presently described invention is not limited to the arrangements and instrumentality shown in the attached drawings.

DETAILED DESCRIPTION OF THE INVENTION

In accordance with embodiments of the presently described technology, an improved mannequin includes artificial organs that are mounted on or attached to a torso of the mannequin in a more reliable and secure manner than existing mannequins. The mannequin body is constructed generally in a human form with a flexible and elastic structure. In an embodiment, the mannequin is inflated with a fluid into a human shape when it is in use.

In an embodiment, the mannequin is in a human female form. The mannequin includes artificial organs each having an orifice mounted on or attached to the main body or torso of the mannequin.

The artificial organs can be in the form of a vagina or anus and mounted in or attached to the area of the lower portion of the mannequin torso. For example, the artificial organs can be mounted on or attached to an area of the mannequin representative of the lower abdomen or crotch area of a human.

In an embodiment, the artificial organs of the vagina and anus are combined into a single unit or a single tube-shaped artificial organ (referred to herein as "tubular organ"). This tubular organ can be made of a material that is more flexible than the material used to create the mannequin torso. In addition, the material used to create the tubular organ is preferably a resilient material.

As described above, the tubular organ can be in an approximately tubular form. That is, the tubular organ can be in the shape of a cylinder with an opening on both ends of the organ. However, the tubular or cylindrical shape of the tubular organ can vary in diameter from one end to the other and/or bend along its length.

The openings in the tubular organ can be adapted to receive human male sexual organs. In an embodiment, one end of the tubular organ is shaped and/or designed to appear as a human female vagina and the other end of the tubular organ is shaped and/or designed to appear as a human female anus. The tubular organ therefore includes a central passage connected to the two openings that can provide a realistic feel of a human orifice.

In an embodiment, at each end of the tubular organ there is a circular ring positioned for supporting and locating the tubular organ on or to the torso of the mannequin.

FIG. 1 illustrates a perspective view of a mannequin 1 with a leg 18 removed from a torso 2 of mannequin 1 in accordance with an embodiment of the presently described invention. Mannequin 1 includes a torso or torso portion 2, a lower torso or lower torso portion 3 and one or more legs 18. While only one leg 18 is shown in FIG. 1 to aid in displaying the features of an embodiment of the invention, the embodiments of the invention are not limited to mannequins 1 with only a single leg 18. Mannequins 1 can include two legs 18 in accordance with the embodiments of the invention. In addition, in an embodiment torso 2 and lower torso 3 can be continuous areas or volumes of mannequin 1. That is, there is no physical separation between torso 2 and lower torso 3. In another embodiment, torso 2 and lower torso 3 can be separate, physically distinct volumes of mannequin 1 that are connected or attached to one another.

In an embodiment, mannequin 1 is in the shape or form of a human. In a preferred embodiment, mannequin 1 is in the shape of a female human. In such embodiments, lower torso 3 is representative of a crotch area of a human and legs 18 are attached to or mounted on mannequin 1 at opposing sides of lower torso 3.

One or more of torso 2, lower torso 3 and legs 18 is made of an elastic material. For example, one or more of torso 2, lower torso 3 and legs 18 is made of a plastic material capable of returning to its original shape after being stretched.

In an embodiment, one or more of torso 2, lower torso 3 and legs 18 is hollow. For example, lower torso 3 is hollow and includes a torso cavity or chamber 5. Lower torso 3 includes a tubular organ 4. In addition and as described in more detail below, lower torso 3 also includes first and second mounting rings 14, 15. In an embodiment of the presently described invention, lower torso 3 includes additional devices or apparatuses. For example, lower torso 3 can include a vibration unit or device 10 and/or an inflatable tube 11. Vibration unit 10 includes any device capable of vibrating the unit 10. Inflatable tube 11 includes any object capable of being inflated. For example, inflatable tube 11 can include a tubular bladder with an air nozzle 12 for inflating and deflating tube 11. Tube 11 can be inflated to provide resistance to a user using mannequin 1 and/or to provide a more realistic shape to mannequin 1.

Tubular organ 4 is tube-shaped artificial organ. In an embodiment, tubular organ 4 is made of a resilient material such as a plastic material. Tubular organ 4 includes first and second ends 6, 8, which include first and second openings 7, 9 of tubular organ 4. In an embodiment, vibration unit 10 can be included in or proximate the tubular middle portion of organ 4.

Figure 2:
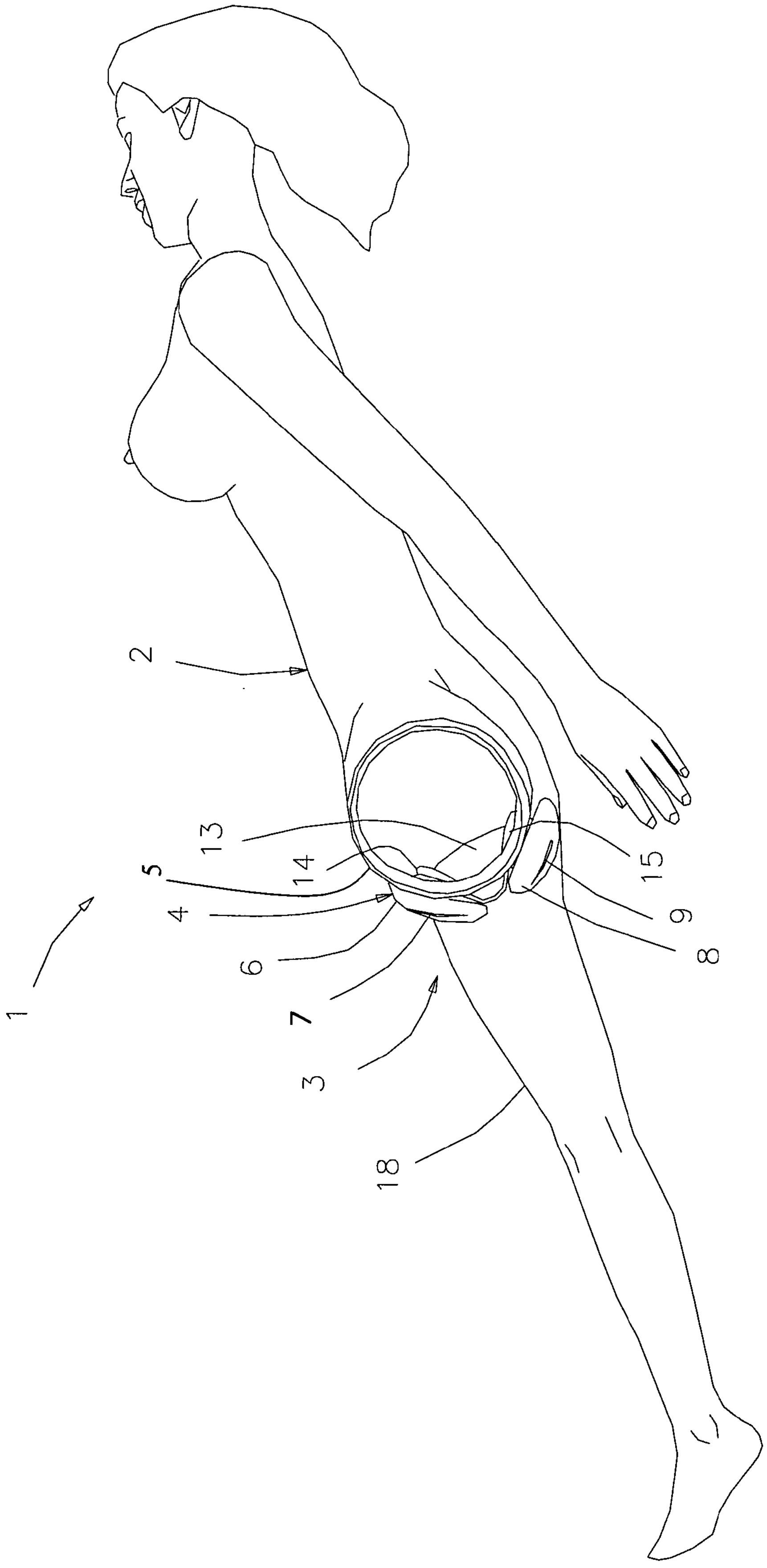
FIG. 2 illustrates a perspective view of the mannequin with the inflatable tube and vibrating unit removed from the torso chamber of the mannequin in accordance with an embodiment of the presently described invention.

In another embodiment of the presently described invention, mannequin 1 does not include vibrating unit 10 or inflatable tube 11. FIG. 2 illustrates a perspective view of mannequin 1 with inflatable tube 11 and vibrating unit 10 removed from torso chamber 5 in accordance with an embodiment of the presently described invention.

Figure 3:
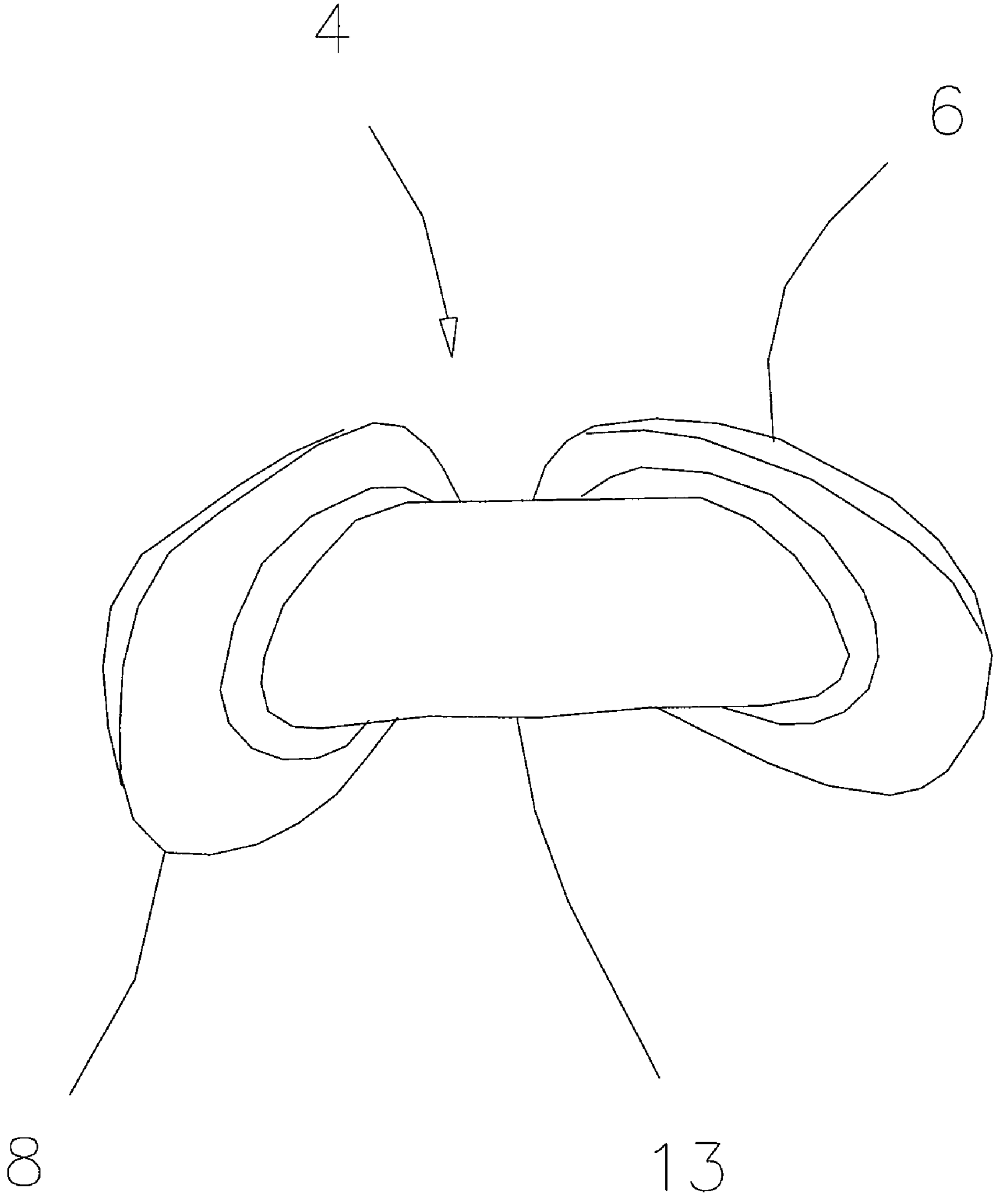
FIG. 3 illustrates a perspective view of the tubular organ in accordance with an embodiment of the presently described invention.
Figure 4:
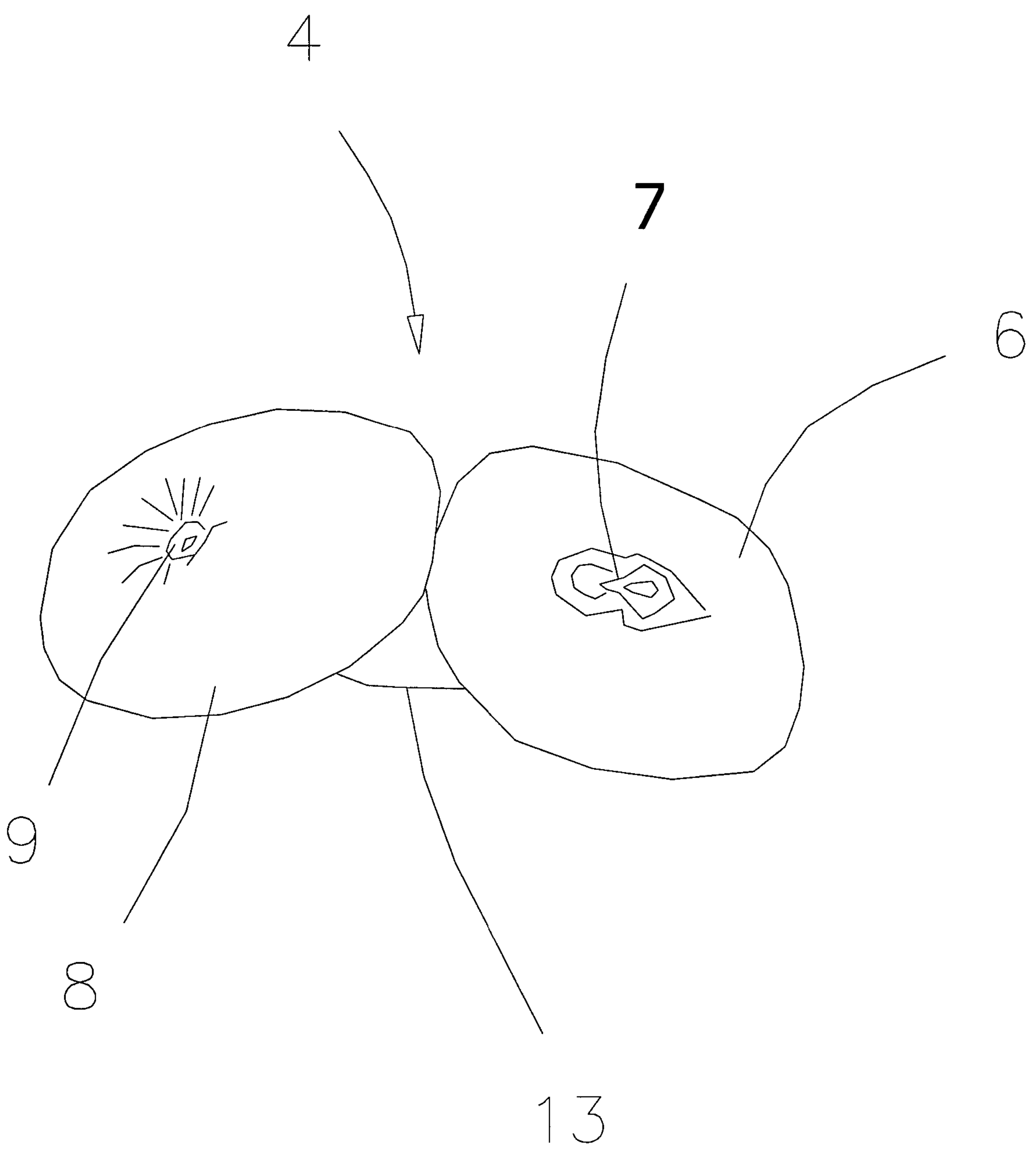
FIG. 4 illustrates another perspective view of the tubular organ in accordance with an embodiment of the presently described invention.

FIGS. 3 and 4 illustrate perspective views of tubular organ 4 in accordance with an embodiment of the presently described invention. As shown in FIGS. 3 and 4, tubular organ 4 includes first and second ends 6, 8, first and second openings 7, 9 and a sleeve 13. In an embodiment, organ 4 is made of a material having resilient properties. First and second ends 6, 8 can be modeled or created so as to resemble orifices of a female. For example, first end 6 can be designed to resemble a vagina or vaginal opening and second end 8 can be designed to resemble an anus or anal opening.

First and second ends 6, 8 each include an opening to the inside of organ 4 and, more specifically, sleeve 13. For example, first end 6 includes first opening 7 and second end 8 includes second opening 9.

Figure 5:
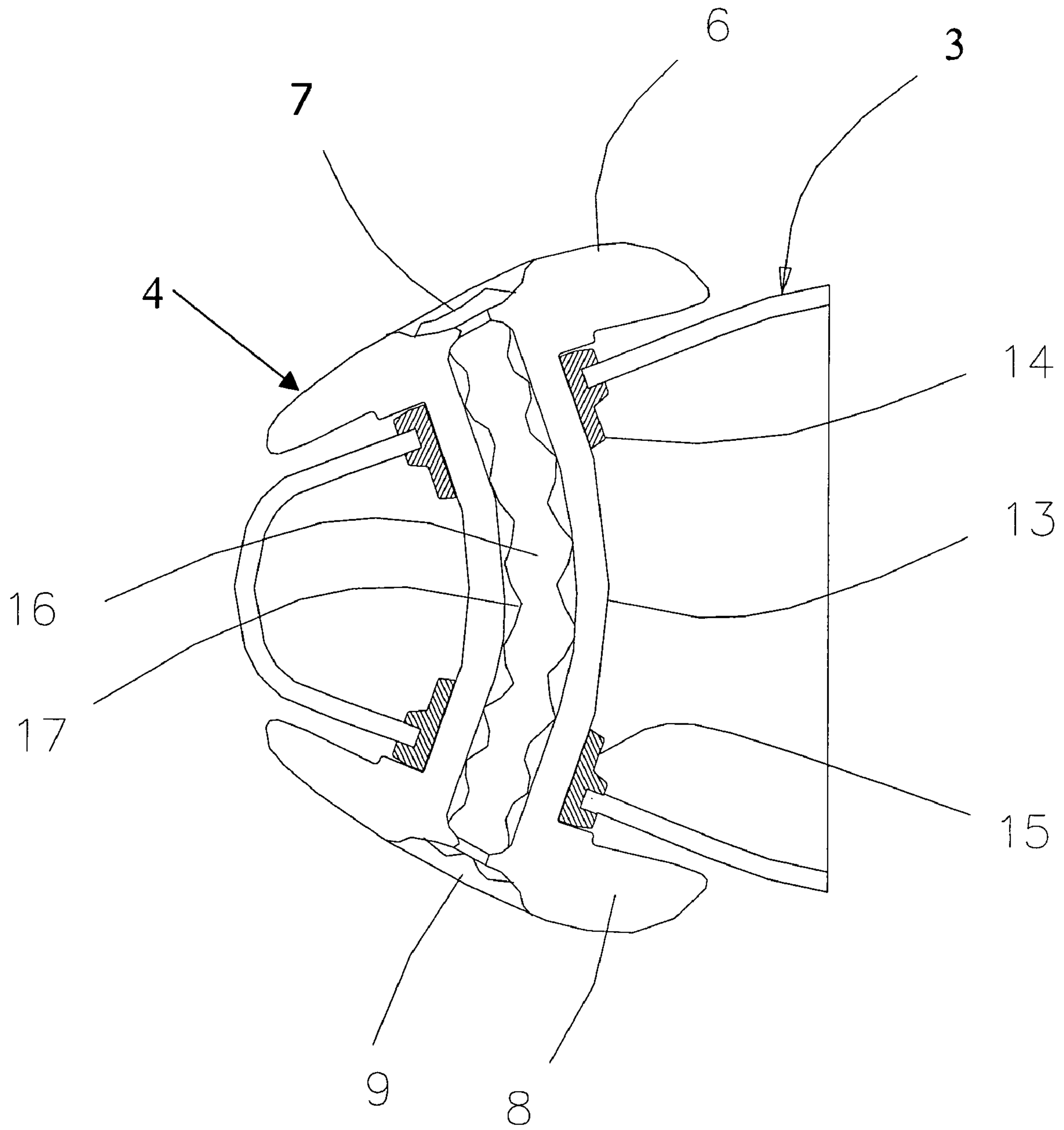
FIG. 5 illustrates a sectional view of the lower torso of the mannequin in accordance with an embodiment of the presently described invention.

FIG. 5 illustrates a sectional view of lower torso 3 of mannequin 1 in accordance with an embodiment of the presently described invention. As shown in FIG. 5, organ 4 includes sleeve 13. Sleeve 13 connects first and second ends 6, 8 and connects first and second openings 7, 9. In doing so, sleeve 13 defines a channel or center passage 16 of organ 4. In an embodiment, sleeve 13 includes a plurality of protrusions 17, or raised objects along the interior surface of sleeve 13. Protrusions 17 can be employed to enhance the tactile feeling to the object penetrated into sleeve 13. In another embodiment, the interior surface of sleeve 13 is smooth.

By providing a continuous channel 16 through organ 4 and between openings 7, 9, the inside passage 16 of organ 4 can be cleaned more easily than existing mannequins. For example, existing mannequins frequently have one or more orifices or openings for penetration by a user. However, these openings frequently are not connected with one another by a channel and merely provide an entrance to a volume with no other opening or exit. In this manner, the interior volumes of existing orifices and openings are difficult to clean before and/or after use of the mannequin. By providing channel 16 from one opening 7 to another 9, the interior volume of organ 4 (that is, channel 16) can be easily cleaned by flushing channel 16 with a fluid.

In an embodiment of the presently described invention, organ 4 and lower torso 3 comprise different materials. For example, organ 4 can comprise a softer, more flexible material than lower torso 3. In order to provide a more reliable connection between organ 4 and lower torso 3, first and second mounting rings 14, 15 are provided. First and second mounting rings 14, 15 can be provided inside two holes or openings in lower torso 3 (where each of the holes are defined by the area through which organ 4 passes through lower torso 3 as shown in FIG. 5). As shown in FIG. 5, rings 14, 15 are provided proximate first and second openings 7, 9 and first and second ends 6, 8. Rings 14, 15 can comprise a rigid material such as a stiff plastic material. In an embodiment, rings 14, 15 comprise a material that is more rigid or stiff than organ 4.

Organ 4 can be connected to each ring 14, 15 by use of an adhesive or by otherwise bonding organ 4 to each ring 14, 15, for example. Rings 14, 15 can be connected to the openings in lower torso 3 by use of an adhesive or by otherwise bonding organ 4 to each ring 14, 15, for example. In another example, rings 14, 15 can be connected to the openings in lower torso 3 by a snap-fit connection. That is, rings 14, 15 can be slightly compressed and inserted into the openings in lower torso 3, followed by releasing rings 14, 15. Once the compression on rings 14, 15 is then released, rings 14, 15 can return to their original shape and be held in place by the openings in lower torso 3.

As shown in FIG. 5, rings 14, 15 provide an intermediary in the mounting of or attachment between organ 4 and lower torso 3. Rings 14, 15 can be varied to adjust the attachment between organ 4 and lower torso 3. For example, the amount of surface area in contact between rings 14, 15 and organ 4 can be varied by changing the size of rings 14, 15. In doing so, the connection or attachment between organ 4 and lower torso 3 is improved. That is, instead of relying on the relatively small amount of surface area between lower torso 3 and organ 4 (that would be used in the absence of rings 14, 15), rings 14, 15 provide an increased amount of surface area, and thus an improved attachment, between rings 14, 15 and organ 4.

In another example, the relative stiffness or flexibility among lower torso 3, organ 4 and/or rings 14, 15 can also be varied. For example, rings 14, 15 can be stiffer or less flexible than organ 4 but less stiff or more flexible than lower torso 3.

Figure 6:
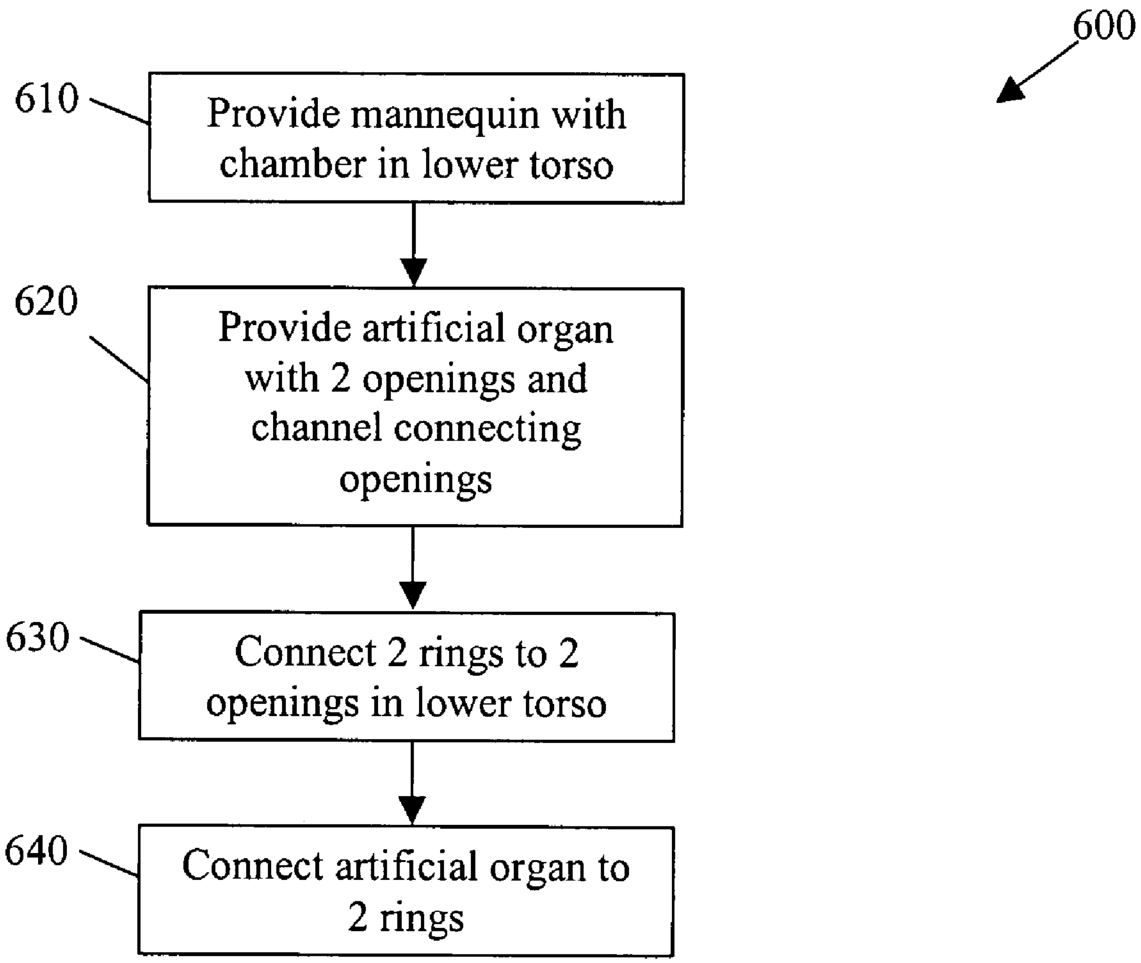
FIG. 6 illustrates a flowchart for a method for providing a more reliable connection between an artificial organ and a mannequin in accordance with an embodiment of the presently described invention.

FIG. 6 illustrates a flowchart for a method 600 for providing a more reliable connection between an artificial organ 4 and a mannequin 1 in accordance with an embodiment of the presently described invention. Method 600 begins at step 610, where a mannequin 1 with a chamber 5 in a lower torso 3 is provided, as described above. Next, at step 620, an artificial organ 4 is provided that includes two openings 7, 9 and a sleeve 13 (which comprises a channel 16 connecting the two openings 7, 9), as described above. Next, at step 630, a mounting ring 14, 15 is connected to each of two openings in lower torso 3, also as described above. Finally, at step 640, artificial organ 4 is connected to each of rings 14, 15. By following method 600, an artificial organ 4 is mounted or attached to mannequin 1.

In another embodiment of the presently described invention, steps 630 and 640 of method 600 are switched in order. That is, step 640 occurs before step 630.

While particular elements, embodiments and applications of the presently described invention have been shown and described, it is understood that the presently described invention is not limited thereto since modifications may be made by those skilled in the technology, particularly in light of the foregoing teaching. It is therefore contemplated by the appended claims to cover such modifications and incorporate those features that come within the spirit and scope of the presently described invention.

The invention claimed is:

1. A mannequin comprising:
a torso defining a chamber; and
an artificial organ comprising:
a first opening and a second opening, and
a sleeve defining a channel connecting the first and second openings; and
a plurality of mounting rings for connecting the artificial organ to the torso.

2. The mannequin of claim 1, wherein the chamber comprises a first hole and a second hole, wherein at least one of the plurality of rings is located inside each of the first and second holes.

3. The mannequin of claim 1, wherein the sleeve comprises a plurality of protrusions along an interior surface of the channel.

4. The mannequin of claim 1, wherein the artificial organ is located inside the chamber.

5. The mannequin of claim 1, wherein the chamber includes a vibration unit.

6. The mannequin of claim 1, wherein the chamber includes an inflatable tube.

7. The mannequin of claim 1, wherein the artificial organ is less rigid than the torso.

8. A mannequin with an attachment between an artificial organ and a torso of the mannequin comprising:
a first mounting ring engaged to the artificial organ and a first hole defined in the torso, wherein the mounting ring is attached to the artificial organ proximate a first opening in the organ and the mounting ring engaged to the torso proximate the first hole.

9. The mannequin of claim 8, wherein the artificial organ further comprises:
a second opening and a sleeve defining a channel, the channel connecting the first and second openings of the organ.

10. The mannequin of claim 9, wherein the sleeve comprises a plurality of protrusions along an interior surface of the channel.

11. The mannequin of claim 9, further comprising:
a second mounting ring engaged to the artificial organ proximate the second opening in the artificial organ and attached to the torso proximate a second hole in the torso.

12. The mannequin of claim 8, wherein the first mounting ring is engaged to the hole in the torso with a snap-fit connection.

13. The mannequin of claim 8, wherein the first opening represents a human orifice.

14. The mannequin of claim 8, wherein the artificial organ is less rigid than the torso.

15. A method for attaching an artificial organ to a mannequin, comprising:
engaging at least one mounting ring to the artificial organ;
inserting the artificial organ and the at least one mounting ring into a hole defined by the mannequin; and
engaging the at least one mounting ring to the hole defined by the mannequin.

16. The method of claim 15, wherein the at least one mounting ring engages the artificial organ proximate at least one of a plurality of openings and along a channel defined by a sleeve that connects the at least one of a plurality of openings.

17. The method of claim 15, wherein the at least one mounting ring is engaged to the hole defined by the mannequin prior to engaging the at least one ring to the artificial organ and inserting the artificial organ into the hole.

18. The method of claim 15, wherein the at least one mounting ring engages the hole defined by the mannequin in a snap-fit connection.

19. The mannequin of claim 1, wherein each of the plurality of rings comprises first and second flange that define an annular channel around an exterior surface of each of the plurality of mounting rings wherein the annular channel is configured to receive the torso.

20. The mannequin of claim 11, wherein:
the first mounting ring comprises a first upper flange and a first lower flange defining a first annular channel around a first exterior surface of the first mounting ring to receive and engage a first perimeter of the first hole of the torso; and
the second mounting ring comprises a second upper flange and a second lower flange defining a second annular channel around an exterior surface of the second mounting ring to receive and engage a second perimeter of the second hole of the torso.

* * * * *

UNITED STATES PATENT AND TRADEMARK OFFICE

CERTIFICATE OF CORRECTION

PATENT NO. : 8,157,723 B2
APPLICATION NO. : 11/712091
DATED : April 17, 2012
INVENTOR(S) : Simon Siu Man Nan It is certified that error appears in the above-identified patent and that said Letters Patent is hereby corrected as shown below:

On the Title page, Item 57 in the Abstract, at line 8: “a plurality of rings a plurality of holes” should read --a plurality of rings and a plurality of holes--

Column 1, lines 52-53: “a plurality of rings a plurality of holes” should read --a plurality of rings and a plurality of holes--

Column 3, line 47: “organ 4 is tube-shaped” should read --organ 4 is a tube-shaped--

Signed and Sealed this
Sixth Day of November, 2012

David J. Kappos
*Director of the United States Patent and Trademark Office*